(12) United States Patent
Jin et al.

(10) Patent No.: US 11,850,388 B2
(45) Date of Patent: Dec. 26, 2023

(54) METHOD FOR TESTING SUITABILITY OF MICRONEEDLE MATERIAL SUITABLE FOR MANUFACTURE EMPLOYING ELONGATION PROCESS, AND MICRONEEDLE MANUFACTURING METHOD COMPRISING SAME

(71) Applicant: RAPHAS CO., LTD., Seoul (KR)

(72) Inventors: Ju Young Jin, Goyang-si (KR); Moon Su Lee, Anyang-si (KR); Tae Hyung Kim, Gimpo-si (KR); Jung Dong Kim, Incheon (KR); Do Hyeon Jeong, Seoul (KR)

(73) Assignee: RAPHAS CO., LTD., Seoul (KR)

( * ) Notice: Subject to any disclaimer, the term of this patent is extended or adjusted under 35 U.S.C. 154(b) by 415 days.

(21) Appl. No.: 17/343,061

(22) Filed: Jun. 9, 2021

(65) Prior Publication Data
US 2021/0290922 A1    Sep. 23, 2021

Related U.S. Application Data

(63) Continuation of application No. PCT/KR2019/007466, filed on Jun. 20, 2019.

(30) Foreign Application Priority Data

Dec. 12, 2018    (KR) .................. 10-2018-0159987

(51) Int. Cl.
*A61M 37/00* (2006.01)
*B29D 99/00* (2010.01)
*G01N 11/02* (2006.01)

(52) U.S. Cl.
CPC .......... *A61M 37/0015* (2013.01); *B29D 99/00* (2013.01); *G01N 11/02* (2013.01); *A61M 2037/0053* (2013.01); *A61M 2205/70* (2013.01)

(58) Field of Classification Search
CPC ...... A61M 2037/0053; A61M 2205/70; A61M 37/0015; G01N 11/02; G01N 11/142; B29D 99/00
See application file for complete search history.

(56) References Cited

U.S. PATENT DOCUMENTS 9,737,247 B2 * 8/2017 Wang .................. A61B 5/14532
10,507,312 B2 * 12/2019 Kim ........................ H01J 37/32
(Continued)

FOREIGN PATENT DOCUMENTS

JP       2005154321 A    6/2005
KR    1020120068516 A    6/2012
(Continued)

OTHER PUBLICATIONS

International Search Report of PCT/KR2019/007466 dated Sep. 23, 2019.

*Primary Examiner* — Andre J Allen
(74) *Attorney, Agent, or Firm* — Dinsmore & Shohl LLP; Yongsok Choi, Esq.

(57) ABSTRACT

A method of manufacturing a microneedle includes selecting and providing a microneedle material whose viscosity/elastic modulus measured for each shear rate using a viscoelasticity measuring equipment falls in a range between a predetermined upper limit and a predetermined lower limit, and manufacturing the microneedle using the microneedle material by an extension process.

8 Claims, 2 Drawing Sheets

(56) References Cited

U.S. PATENT DOCUMENTS

| | | |
|---|---|---|
| 2002/0138049 A1 | 9/2002 | Allen et al. |
| 2008/0157421 A1 | 7/2008 | Mukai et al. |
| 2013/0123707 A1 | 5/2013 | Determan et al. |
| 2016/0166184 A1* | 6/2016 | Teng ................ A61B 5/150969 600/347 |

FOREIGN PATENT DOCUMENTS

| | | | |
|---|---|---|---|
| KR | 20130058012 A | * | 6/2013 |
| KR | 101285085 B1 | | 7/2013 |
| KR | 20140001956 A | * | 1/2014 |
| KR | 101435888 B1 | | 9/2014 |
| KR | 101754309 B1 | | 7/2017 |

* cited by examiner

METHOD FOR TESTING SUITABILITY OF MICRONEEDLE MATERIAL SUITABLE FOR MANUFACTURE EMPLOYING ELONGATION PROCESS, AND MICRONEEDLE MANUFACTURING METHOD COMPRISING SAME

CROSS-REFERENCE TO RELATED APPLICATION

This application is a continuation of International Application No. PCT/KR2019/007466 filed on Jun. 20, 2019, which claims priority to Korean Patent Application No. 10-2018-0159987 filed on Dec. 12, 2018, the entire contents of which are herein incorporated by reference.

TECHNICAL FIELD

The present disclosure relates to a method of testing suitability of a microneedle material suitable for manufacturing a microneedle by an extension process, and a microneedle manufacturing method including the suitability testing method.

BACKGROUND

Although a great number of drugs and bioactive substances for treating diseases has been developed, it is challenging to deliver the drugs and bioactive substances into the body due to a biological barrier, for example, skin, oral mucosa, and brain-blood barrier and thus, problems regarding passing through the biological barrier and delivery efficiency of drugs still remain.

In general, drugs and bioactive substances are orally administered in the form of tablets or capsules. However, various drugs are digested or absorbed in the gastro-intestinal tract or lost due to a liver mechanism and accordingly, the drugs and bioactive substances may not be efficiently delivered. In addition, several drugs pass through intestinal mucous membrane and may not be effectively spread. Patient's compliance is also an issue (for example, if a patient needs to take medicine in a regular interval, or critical patents who cannot take medicine).

Other general way of delivering drugs and bioactive substances is a use of conventional needles. It is a more efficient way than oral administration, however, may cause pain on injection sites, a local damage on skin, bleeding, and disease infection on injection sites.

In order to solve problems of oral administration and subcutaneous injection, transdermal administration using patches are used. In the transdermal administration using patches, patient compliance is high, and drug level in blood remains steady.

In order to solve the above problems, various micro structures including microneedles are developed. The microneedles developed until the present are mainly used in delivering drugs in the body, blood-gathering, and detecting analyte in the body.

Unlike conventional needles, the microneedles should not cause pain and injury when they penetrate the skin. For such painless skin penetration, the diameter of the upper end portion of the needle is a matter to be considered for minimal invasiveness. In addition, the microneedle should have a physical hardness sufficient to penetrate the stratum corneum with a thickness of 10-20 μm. Further, the microneedles should have a length sufficient to reach the capillary vessel for a high efficient drug delivery.

Various types of microneedles have been developed after the conventional in-plane type of microneedle ("Silicon-Processed Microneedles", Journal of Microelectrochemical System 8, 1999) has been proposed. A method of producing an out-of-plane type solid microneedle based on an etching method (U.S. Patent Application Publication No. 2002138049, entitled "MICRONEEDLE DEVICES AND METHODS OF MANUFACTURE AND USE THEREOF") produces solid silicone microneedles with a diameter of 50-100 μm and a length of 500 μm, but it is impossible to realize the painless skin penetration, and it was difficult to deliver a drug and a cosmetic component to a target site.

Further, a method of manufacturing biodegradable polymer microneedles by etching glass or forming a mold with photolithography was disclosed by Prausnitz at the University of Georgia in the United States. Using this method, it has an advantage of freely loading a drug which can be produced in a capsule form, but the hardness of the micro needle decreases when an amount of drug loading increases, and thus there is a limit in application to drugs requiring a large amount of medication.

In 2005, an absorbable microneedle was manufactured by Nano Device and Systems Inc. (Japanese Patent Laid-Open Publication No. 2005154321).

Such an absorbable microneedle is used in drug delivery or cosmetics without removing the microneedle inserted intradermally. According to the above-described method, a composition prepared by mixing maltose with a drug is applied to a mold and then solidified to thereby manufacture a microneedle. The above Japanese patent discloses a manufacturing of an absorbable microneedle for transdermal absorption of drugs, but skin penetration of the absorbable microneedle is accompanied by pain. In addition, due to a technical limitation to the manufacture of a mold, it was difficult to manufacture a microneedle having an upper end portion of a suitable diameter causing no pain and a length required for effective drug delivery, that is, a length equal to or greater than 1 mm.

A biodegradable microneedle suggested by Prausnitz at the University of Georgia in the United States in 2008 was manufactured using a polydimethylsiloxane (PDMS) mold and a material prepared by mixing polyvinylpyrrolidone (PVP) with methacrylic acid (MAA). Also, a microneedle was manufactured by injecting carboxymethylcellulose into a pyramid-structure mold. However, the method using a mold has a limitation in that a new mold and frame should be manufactured through a complicated process so as to adjust a diameter and a length of the microneedle, and further has a disadvantage in that a process of injecting a material into a mold to manufacture the microneedle is a complicated and time-consuming process.

In 2008, an apparatus and a method for manufacturing a skin needle using a pin structure were disclosed through U.S. patent filed by Mukai et al. of Japan (U.S. Patent Publication No. 20080157421A1). This method employs a technique of pulling a viscous substance with a pin structure by heating the viscous substance at a base of a substrate. Since this technique pulls the material, which is melted by heat or has viscosity, with the pin structure, limitations still remained in an increase of a manufacture cost due to a process for newly manufacturing the pin structure depending on a desired pattern, and difficulty in loading various thermosensitive biopharmaceuticals (a hormone, a vaccine, other protein drug, and the like) due to the heating process.

Meanwhile, the skin is composed of a stratum corneum (<20 μm), an epidermis (<100 μm), and a dermis (300 to 2,500 μm), which are sequentially stacked from an outer layer of the skin. Therefore, in order to deliver drugs and bioactive substances to a specific skin layer with no pain, a microneedle needs to be manufactured to have a diameter equal to or greater than approximately 30 μm at an upper end portion, an effective length of 200 to 2,000 μm, and a sufficient hardness to skin penetration such that the drugs and skin care ingredients may be effectively delivered. In addition, in order to deliver drugs, bioactive substances and the like through a biodegradable solid microneedle, it could exclude a process, which may destroy activities of the drugs and the bioactive substances, including a high heat treatment, an organic solvent treatment and the like from the microneedle manufacturing process.

A conventional solid microneedle is limited to be manufactured with a material including a silicon, polymers, a metal, a glass and the like due to a limitation of the manufacturing method, and has disadvantages in that drug degeneration, insufficient hardness, a loss of a drug, and the like occur according to a complicated and highly time-consuming manufacturing process due to a manufacturing method using a molding technique. Consequently, there are ongoing demands for a method of manufacturing a microneedle, wherein the method is capable of implementing a sufficient hardness with no specific limitation to a material while having a thin diameter to realize skin penetration with no pain and a sufficient length to deeply penetrate into a skin, and minimizing a loss of a drug.

To address the problems as described above, the present inventors proposed a new microneedle manufacturing method using a droplet air-born blowing. Various microneedle manufacturing methods using such a droplet-born air blowing proposed by the present inventors have been applied to the Korean Intellectual Property Office as KR 10-2009-094018, KR 10-2010-030127, KR 10-2010-130169, KR 10-2012-117936, KR 10-2015174066, KR 10-2016-061903, and the like. The disclosures of Korean Patent Applications applied by the present inventors are considered to be incorporated herein in their entirety by references.

The microneedle manufacturing method, which has been proposed by the present disclosure, and uses the droplet-born air blowing different from a conventional molding or micro-molding employs a viscous composition as a material of a microneedle. The reason for employing the viscous substance is to manufacture the microneedle by air blowing drying after extension subsequent to contact.

Meanwhile, in addition to the above-described droplet-born air blowing, microneedle manufacturing methods using some types of extension processes are known in the field of the present disclosure. One of the extension processes is a process called centrifugal lithography process. In such a centrifugal lithography process, a viscous composition is provided to a rotator. The viscous composition is extended by virtue of a centrifugal force generated when the rotator rotates. An outer end portion of the extended viscous composition is brought into contact with a plate located outside the rotator so that the viscous composition is formed and solidified in an hourglass shape. The intermediate portion of the hourglass shape is cut to form two microneedles. Compared with the droplet-born air blowing described above, the method using such an extension process features that a structure of the viscous composition is solidified while moisture of the viscous composition is evaporated during the extension by the centrifugal force without an additional blowing solidification process.

As described above, there is a difference between the droplet-born air blowing and the centrifugal lithography process in terms of the presence or absence of the blowing solidification process. However, the droplet-born air blowing and the centrifugal lithography process are the same in manufacturing a microneedle by the extension of the viscous composition. This feature is different from that of the molding process described above. The present disclosure is based on the extension process rather than the molding process. The extension process employed in the present disclosure is to be taken as encompassing all known methods of forming microneedles by the extension of the viscous composition, such as the droplet-born air blowing and the centrifugal lithography process described above, and the like.

Various substances are available as the viscous composition used to manufacture the microneedle in the extension process as described above. For example, the viscous composition may include a hyaluronic acid and a salt thereof, polyvinyl pyrrolidone, cellulose polymer, dextran, gelatin, glycerin, polyethylene glycol, polysorbate, propylene glycol, povidone, carbomer, gum ghatti, guar gum, glucomannan, glucosamine, dammer resin, rennet casein, locust bean gum, microfibrillated cellulose, psyllium seed gum, xanthan gum, arabino galactan, arabic gum, alginic acid, gelatin, gellan gum, carrageenan, karaya gum, curdlan, chitosan, chitin, tara gum, tamarind gum, tragacanth gum, furcelleran, pectin, or pullulan. The present disclosure is not limited to the above substances, and various viscous substances other than those described above may be used. Viscous substances disclosed in the specifications of Korean Patent Applications, which are related to the aforementioned droplet-born air blowing proposed by the present inventors may belong to the candidate group usable as a viscous composition, which is a material of the microneedle.

However, even if materials having viscosity are used, it cannot be said that they are suitable for the extension process. Furthermore, the material suitable for the extension process do not include only materials determined to be suitable for forming a microneedle as viscous composition. The material suitable for the extension process may further include various bioactive drugs, and a maxing ratio of the bioactive drugs may also be changed. When other components are additionally included in the existing material whose suitability has been confirmed for the formation of a needle or a mixing ratio thereof is changed, the suitability for the formation of the needle needs to be evaluated again.

Whether or not a material is suitable for forming a microneedle with an extension process was confirmed through an evaluation process performed after putting the material into the actual process to form microneedles having various lengths.

SUMMARY

An object of the present disclosure is to provide a microneedle material suitable for manufacturing a microneedle by an extension process, a microneedle manufacturing method using the microneedle material, a method of testing suitability of the microneedle material, and a microneedle manufacturing method including the suitability testing method.

A method of manufacturing a microneedle according to an embodiment of the present disclosure includes selecting and providing a microneedle material whose viscosity/elastic modulus measured for each shear rate using a viscoelasticity measuring equipment falls in a range between a predetermined upper limit and a predetermined lower limit, and manufacturing the microneedle using the selected and provided microneedle material by an extension process.

The method of manufacturing the microneedle material may further include checking whether or not the measured viscosity/elastic modulus is continuously decreased as the shear rate increases to select the microneedle material.

In some embodiments, a method of testing a suitability of a microneedle material according to an embodiment of the present disclosure may include measuring a viscosity/elastic modulus of a microneedle material for each shear rate using a viscoelasticity measuring equipment; checking whether all values of the viscosity/elastic modulus measured for each shear rate fall in a range between a predetermined upper limit and a predetermined lower limit; and when the all values of the viscosity/elastic modulus measured for each shear rate are determined to fall in the range between the predetermined upper limit and the predetermined lower limit, determining that the microneedle material is suitable for forming the microneedle by an extension process.

The above method of testing the suitability of the microneedle material may further include checking whether or not the measured viscosity/elastic modulus is continuously decreased as the shear rate increases to select the microneedle material In both the method for manufacturing the microneedle and the method of testing the suitability of the micro needle material, the predetermined upper limit and the predetermined lower limit of the viscosity/elastic modulus measured for each shear rate may be set as follows.

47.17 and 6.67 for the shear rate of 0.03 1/s,
35.07 and 4.86 for the shear rate of 0.04 1/s,
25.37 and 3.77 for the shear rate of 0.06 1/s,
18.40 and 3.06 for the shear rate of 0.10 1/s,
13.47 and 2.56 for the shear rate of 0.16 1/s,
10.06 and 2.18 for the shear rate of 0.25 1/s,
7.71 and 1.88 for the shear rate of 0.40 1/s,
5.99 and 1.65 for the shear rate of 0.63 1/s,
4.71 and 1.46 for the shear rate of 1.01 1/s,
4.08 and 1.32 for the shear rate of 1.62 1/s, and
2.89 and 1.09 for the shear rate of 2.59 1/s.

The predetermined upper limit and the predetermined lower limit of the viscosity/elastic modulus measured for each shear rate were derived through experiments conducted repeatedly by the present inventors. These values are new boundary values that are not known to persons skilled in the art prior to the present disclosure. By applying a criteria based on these boundary values, it is possible to accurately discriminate a microneedle material suitable for an extension process in an easier manner.

Further, the present disclosure may further include additional features other than the above features.

According to the present disclosure, it is possible to provide a microneedle material suitable for manufacturing a microneedle by an extension process, a microneedle manufacturing method using the microneedle material, a method of testing suitability of the microneedle material, and a microneedle manufacturing method including the suitability testing method.

More specifically, according to the present disclosure, it is possible to provide a microneedle material whose manufacturing suitability is confirmed in advance without performing an actual extension process on the microneedle material to form a microneedle, and provide the microneedle manufacturing method using such a microneedle material. Further, according to the present disclosure, in a case in which a new material to be used as the microneedle material is selected, it is possible to provide the method of testing the suitability of the new substance before performing a process on the new substance. Further, it is possible to provide the microneedle manufacturing method including the suitability testing method. Therefore, even if the new substance is added or a mixing ratio thereof is changed, it is possible to determine the suitability of the new substance before performing the process on the new substance.

As described above, by providing the microneedle material having new features, the method of testing the micro needle material, the microneedle manufacturing method using the microneedle material, or the microneedle manufacturing method including the testing method, it is possible to determine the microneedle material suitable for the extension process before performing the extension process, thereby increasing the efficiency of the overall process. By objectively and efficiently discriminating a material suitable for the extension process, it is possible to improve the quality of the microneedle produced by the extension process.

DETAILED DESCRIPTION

In the following detailed description of the present disclosure, references are made to the accompanying drawings that show, by way of illustration, specific embodiments in which the present disclosure may be practiced. These embodiments are described in sufficient detail to enable those skilled in the art to practice the present disclosure. It is to be understood that the various embodiments of the present disclosure, although different from each other, are not necessarily mutually exclusive. For example, specific shapes, structures and characteristics described herein may be implemented as modified from one embodiment to another without departing from the spirit and scope of the present disclosure. Furthermore, it shall be understood that the positions or arrangements of individual elements within each of the embodiments may also be modified without departing from the spirit and scope of the present disclosure. Therefore, the following detailed description is not to be taken in a limiting sense, and the scope of the present disclosure is to be taken as encompassing the scope of the appended claims and all equivalents thereof.

Hereinafter, various preferred embodiments of the present disclosure will be described in detail with reference to the accompanying drawings to enable those skilled in the art to easily implement the present disclosure.

Figure 1:
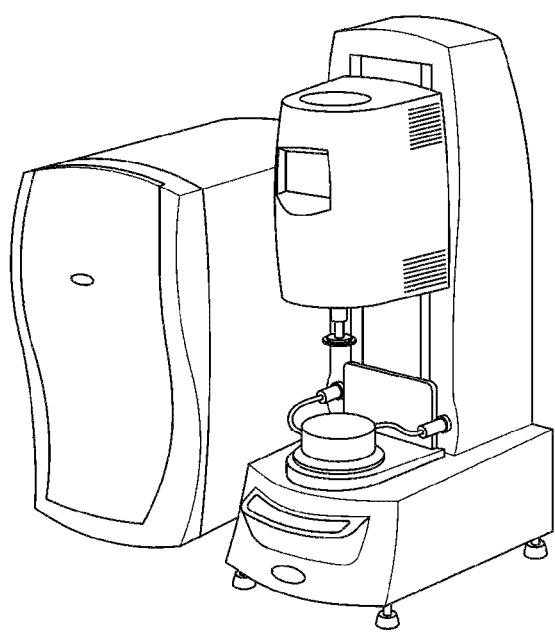
FIG. 1 is a view illustrating a viscoelasticity measuring equipment used in a method of testing suitability of a microneedle material according to the present disclosure.

FIG. 1 is a view illustrating a viscoelasticity measuring equipment used in a method of testing suitability of a microneedle material according to the present disclosure. The viscoelasticity measuring equipment as illustrated in FIG. 1 is referred to as a rheometer in the related art. The rheometer is an equipment for measuring viscoelasticity of a sample by loading the sample between an upper plate configured to minimize friction using an air bearing and a fixed lower plate.

Prior to measure the viscoelasticity of the sample, a friction force of the equipment is measured to eliminate friction of the equipment itself during the actual viscoelasticity measurement of the sample. The upper plate may be flat, conical, or the like in shape. The shape and size of the used upper plate may vary according to the viscosity or other characteristics of the sample. For example, when a material such as water having a very low viscosity is measured, a plate having a relatively large area needs to be used so as to obtain resistance of a measurable level. A sample is loaded between two parallel plates, between a conical device and a plate, or between other similar geometries, such as cup&bob system. When a torque is applied to the upper plate, a rotational shear stress is applied to a substance, and the resulting strain or strain rate (shear rate) is measured. Measurement conditions for measuring viscoelastic properties of materials disclosed herein using the viscoelasticity measuring equipment illustrated in FIG. 1, namely the rheometer, are as follows.

Temperature: 25 degrees C.
Geometry interval: 1 mm
Shear rate: 0.03 to 2.59 l/s
Sample amount: 0.3 mL
Used plate: flat plate having a diameter of 20 mm Unique values of the materials measured by the present inventors using the viscoelasticity measuring equipment illustrated in FIG. 1 are referred to as tangent of delta values, which may be simply referred to as "tan delta values". The present inventors have found that the tan delta value of a viscous composition determines whether a microneedle can be molded using the corresponding viscous composition or not and has a correlation with a (maximum) length of the moldable needle. When a novel raw substance is selected or a mixing ratio of an existing substance is selected to manufacture a microneedle, a microneedle molding feasibility may be determined in advance by measuring a tan delta value of a viscous composition.

A polymer is a viscoelastic substance having both viscosity and elasticity. In other words, a substance having a perfect viscosity varies in shape without resistance to an external force. Meanwhile, a substance having a perfect elasticity strongly resists to the external force and returns to its original state immediately when the external force disappears. A property of the polymer is in between the properties of the two substances described above. As an example, a rubber ball is assumed. When the rubber ball falls to the floor, it bounces to a point lower than its original height. Such a bouncing property is elasticity. The reason why the ball cannot return to its original height is that the ball lost the energy to bounce back to its original height. In other words, the reason for this is that the power of the ball is extinguished outward in the form of heat. Such a property is viscosity.

The tan delta value described above is defined by viscosity/elastic modulus of a material. The fact that the tan delta value is small means that the elasticity is strong and thus the elastic modulus is greater. The fact that the tan delta value is large means that the viscosity is high and thus the viscosity is greater.

Figure 2:
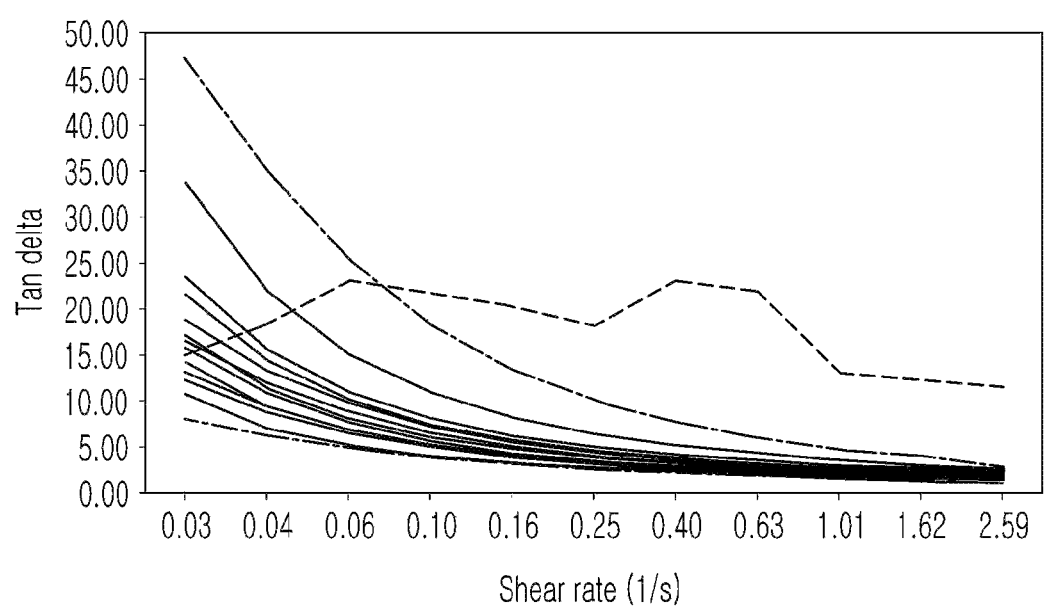
FIG. 2 is a graph illustrating measurement results obtained by measuring tan delta values of various materials, with the shear rate 1/s of the viscoelasticity measuring equipment as the horizontal axis, and the tan delta value as the vertical axis.

FIG. 2 is a graph illustrating measurement results obtained by measuring tan delta values of various materials, with the shear rate l/s of the viscoelasticity measuring equipment as the horizontal axis, and the tan delta value as the vertical axis. The substances used in the experiment illustrated in FIG. 2 were prepared by mixing a high-molecular-weight hyaluronic acid and a low-molecular-weight hyaluronic acid with various mixing ratios.

The dotted line or dashed-dotted lines in the graph of FIG. 2 indicate transitions of tan delta values of substances unsuitable for forming a microneedle. Solid lines in the graph of FIG. 2 indicate transitions of tan delta values of materials suitable for forming a microneedle.

Referring to FIG. 2, it is possible to confirm the features of variation in tan delta values with an increase in shear rates of the materials suitable for forming the microneedle.

The first feature is that the tan delta value decreases as the shear rate increases. One of the materials unsuitable for forming the microneedle, which is illustrated by the dotted line, shows a feature that the tan delta value increases until a particular shear rate (approximately 0.06 l/s) and decreases after the particular shear rate. The material exhibiting such a behavior was found to be a material that is unsuitable for forming the microneedle in the extension process.

The second feature is that the tan delta value needs to fall within a specific range. In the graph of FIG. 2, there are shown two dashed-dotted lines representing that the tan delta value decreases as the shear rate increases. Transitions of the two dashed-dotted lines show that the tan delta value decreases as the shear rate increases, but respective values fall outside a range suitable for forming the microneedle.

The present inventors conducted repeated experiments to obtain an upper limit and a lower limit corresponding to the second feature with respect to the hyaluronic acid having various molecular weights. The results are illustrated in FIG. 3 in the form of graph.

Figure 3:
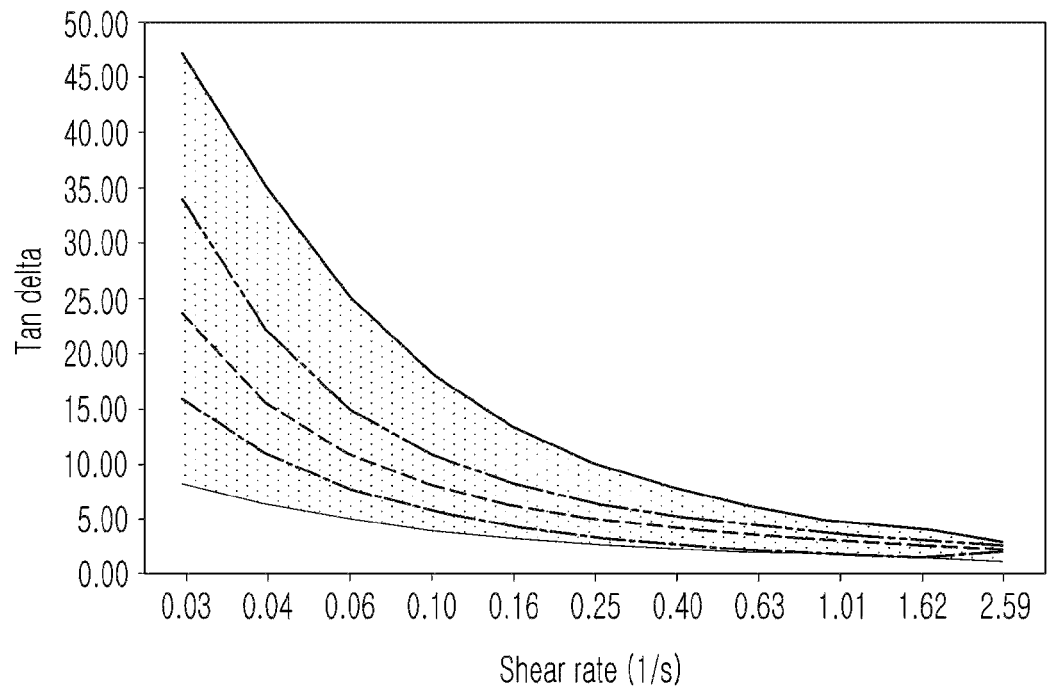
FIG. 3 is a graph illustrating a tan delta range in which a manufacturing suitability is confirmed by an extension process.

FIG. 3 is a graph illustrating a tan delta range in which a manufacturing suitability of the substance by the extension process is confirmed.

In the graph illustrated in FIG. 3, the uppermost solid line and the lowermost solid line indicate the upper limit and the lower limit, respectively. Materials having tan delta values existing in a region between the upper limit and the lower limit were found to be ones suitable for forming a microneedle.

In the graph illustrated in FIG. 3, the upper limit and the lower limit of the tan delta values suitable for forming the microneedle, which are measured for each shear rate, are as follows.

For the shear rate of 0.03 l/s, the upper limit is 47.17 and the lower limit is 6.67, For the shear rate of 0.04 l/s, the upper limit is 35.07 and the lower limit is 4.86, For the shear rate of 0.06 l/s, the upper limit is 25.37 and the lower limit is 3.77, For the shear rate of 0.10 l/s, the upper limit is 18.40 and the lower limit is 3.06, For the shear rate of 0.16 l/s, the upper limit is 13.47 and the lower limit is 2.56, For the shear rate of 0.25 l/s, the upper limit is 10.06 and the lower limit is 2.18, For the shear rate of 0.40 l/s, the upper limit is 7.71 and the lower limit is 1.88, For the shear rate of 0.63 l/s, the upper limit is 5.99 and the lower limit is 1.65, For the shear rate of 1.01 l/s, the upper limit is 4.71 and the lower limit is 1.46, For the shear rate of 1.62 l/s, the upper limit is 4.08 and the lower limit 1.32, and For the shear rate of 2.59 l/s, the upper limit is 2.89 and the lower limit is 1.09.

All the lines in FIG. 3 illustrate the measurement results obtained by measuring the tan delta values of the hyaluronic acids, wherein lines in the graph show the measurement results of hyaluronic acids having different molecular weights. In FIG. 3, the uppermost solid line shows the hyaluronic acid having the lowest molecular weight, and the lowermost solid line shows the hyaluronic acid having the highest molecular weight. As is apparent from the results of FIG. 3, the higher the molecular weight, the smaller the variation in the tan delta value for the shear rate, and the lower the molecular weight, the greater the variation in tan delta value for the shear rate. More specifically, in the graph of FIG. 3, the hyaluronic acid (the hyaluronic acid having the smallest molecular weight) having the largest variation in tan delta value for the shear rate and the hyaluronic acid (the hyaluronic acid having the highest molecular weight) having the smallest variation in tan delta value for the shear rate have molecular weights of 450 kDa, 510 kDa, 530 kDa, 540 kDa, 550 kDa.

FIG. 3 shows the results of experiments conducted to determine whether the microneedle can be molded by the extension process by measuring the tan delta values of the hyaluronic acids having different molecular weights. The present inventors conducted experiments on various substances other than the hyaluronic acid to confirm whether the same range of tan delta values can be used to determine the molding feasibility of the microneedle by the extension process. The results are illustrated in FIG. 4.

Figure 4:
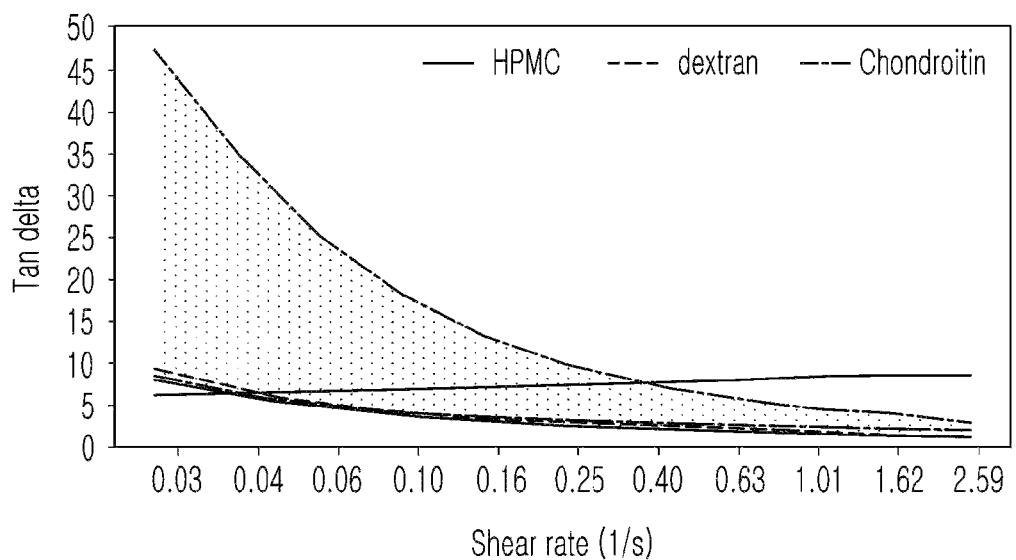
FIG. 4 is a graph illustrating measurement results obtained by measuring tan delta values of various high-molecular-weight substances other than a hyaluronic acid.

FIG. 4 is a graph illustrating measurement results of tan delta values of various high-molecular-weight substances other than the hyaluronic acid.

In the graph illustrated in FIG. 4, the tan delta values of various high-molecular-weight substances measured for each shear rate are as follows.

0.03 l/s: HPMC 4.95, Dextran 7.52, Chondroitin 6.7, PVP 23.47, 0.04 l/s: HPMC 5.00, Dextran 5.39, Chondroitin 4.89, PVP 15.61, 0.06 l/s: HPMC 5.13, Dextran 4.03, Chondroitin 3.8, PVP 10.94, 0.10 l/s: HPMC 5.33, Dextran 3.09, Chondroitin 3.09, PVP 8.11, 0.16 l/s: HPMC 5.59, Dextran 2.44, Chondroitin 2.59, PVP 6.28, 0.25 l/s: HPMC 5.87, Dextran 1.98, Chondroitin 2.21, PVP 5.05, 0.40 l/s: HPMC 6.14, Dextran 1.68, Chondroitin 1.91, PVP 4.18, 0.63 l/s: HPMC 6.41, Dextran 1.32, Chondroitin 1.68, PVP 3.54, 1.01 l/s: HPMC 6.72, Dextran 1.17, Chondroitin 1.49, PVP 3.10, 1.62 l/s: HPMC 6.89, Dextran 1.14, Chondroitin 1.35, PVP 2.58, and 2.59 l/s: HPMC 6.97, Dextran 1.11, Chondroitin 1.12, PVP 2.05

An object of the experiments illustrated in FIG. 4 is to determine whether the same criteria can be applied to various high-molecular-weight substances other than the hyaluronic acid in determining the molding feasibility of the microneedle by the extension process based on the tan delta values.

To this end, viscoelasticities of four substances of HPMC (HydroxyPropyl MethylCellulose), Dextran, Chondroitin, PVP (polyvinylpyrrolidone) were measured. The measured viscoelasticity of HPMC was found to fall out of the moldable range, which did not meet a moldability criteria, whereas the measured viscoelasticities of Dextran, Chondroitin and PVP were found to meet the moldability criteria. Among these four substances, HPMC, Dextran and Chondroitin belong to the polysaccharide family, but PVP belongs to the group of a high-molecular-weight substance rather than the polysaccharide.

In FIG. 4, the range of the tan delta values used for determining the molding feasibility is illustrated. The transitions of the measured tan delta values of the aforementioned four substances are indicated by different types of lines, respectively. In the case of HPMC, the tan delta value thereof was confirmed to fall out of a predetermined tan delta value range, and was determined not meet the moldability criteria because it does not show the behavior that the tan delta value continuously decreases as the shear rate increases unlike other three substances.

In practice, microneedle molding was performed by the extension process using respective substances as materials. As a result, the same conclusion was obtained as expected based on the measured tan delta values. That is, in practice, the material of HPMC was not suitable for forming the microneedle, whereas the materials of Dextran, Chondroitin and PVP were suitable for forming the microneedle.

The above experiments show that the tan delta value can be used as the moldability criteria of the microneedle by the extension process, and show that the criteria can be generally applied to various high-molecular-weight substances other than the hyaluronic acid.

As described above, the correlation between the inherent viscoelastic property (more specifically, the tan delta value) of the microneedle material and the molding feasibility of the microneedle was confirmed.

While the present disclosure has been described in the foregoing by way of embodiments and drawings which are defined with specific matters such as specific components and the like, this is only the one provided to aid in a more general understanding of the present disclosure, and the present disclosure is not limited to the above embodiments, and various modifications and variations can be made from the substrate to those skilled in the art to which the present disclosure pertains.

Accordingly, the spirit of the present disclosure should not be defined as limited to the embodiments described above, and all that have been equivalently or equivalently modified with the claims to be described below, as well as those to be within the scope of the spirit of the present disclosure.

What is claimed is:

1. A method of manufacturing a microneedle, the method comprising:
   selecting and providing a microneedle material whose viscosity/elastic modulus measured for each shear rate using a viscoelasticity measuring equipment falls in a range between a predetermined upper limit and a predetermined lower limit; and
   manufacturing the microneedle using the selected and provided microneedle material by an extension process.

2. A method of manufacturing a microneedle, the method comprising:
   selecting and providing a microneedle material whose viscosity/elastic modulus measured for each shear rate using a viscoelasticity measuring equipment falls in a range between a predetermined upper limit and a predetermined lower limit, wherein the viscosity/elastic modulus measured for each shear rate continuously decreases as the shear rate increases; and manufacturing the microneedle using the microneedle material by an extension process.

3. The method of claim 1, wherein the predetermined upper limit and the predetermined lower limit of the viscosity/elastic modulus measured for each shear rate are
47.17 and 6.67 for the shear rate of 0.03 1/s,
35.07 and 4.86 for the shear rate of 0.04 1/s,
25.37 and 3.77 for the shear rate of 0.06 1/s,
18.40 and 3.06 for the shear rate of 0.10 1/s,
13.47 and 2.56 for the shear rate of 0.16 1/s,
10.06 and 2.18 for the shear rate of 0.25 1/s,
7.71 and 1.88 for the shear rate of 0.40 1/s,
5.99 and 1.65 for the shear rate of 0.63 1/s,
4.71 and 1.46 for the shear rate of 1.01 1/s,
4.08 and 1.32 for the shear rate of 1.62 1/s, and
2.89 and 1.09 for the shear rate of 2.59 1/s.

4. A method of testing a suitability of a microneedle material, the method comprising:
measuring a viscosity/elastic modulus of the microneedle material for each shear rate using a viscoelasticity measuring equipment;
checking whether all values of the viscosity/elastic modulus measured for each shear rate fall in a range between a predetermined upper limit and a predetermined lower limit; and
when the all values of the viscosity/elastic modulus measured for each shear rate are determined to fall in the range between the predetermined upper limit and the predetermined lower limit, determining that the microneedle material is suitable for forming a microneedle by an extension process.

5. A method of testing a suitability of a microneedle material, the method comprising:
measuring a viscosity/elastic modulus of the microneedle material for each shear rate using a viscoelasticity measuring equipment;
checking whether all values of the viscosity/elastic modulus measured for each shear rate fall in a range between a predetermined upper limit and a predetermined lower limit;
determining whether the all values of the viscosity/elastic modulus measured for each shear rate continuously decrease as the shear rate increases; and
when the all values of the viscosity/elastic modulus measured for each shear rate is determined to continuously decrease as the shear rate increases, determining that the microneedle material is suitable for forming a microneedle by an extension process.

6. The method of claim 4, wherein the predetermined upper limit and the predetermined lower limit of the viscosity/elastic modulus measured for each shear rate are
47.17 and 6.67 for the shear rate of 0.03 1/s,
35.07 and 4.86 for the shear rate of 0.04 1/s,
25.37 and 3.77 for the shear rate of 0.06 1/s,
18.40 and 3.06 for the shear rate of 0.10 1/s,
13.47 and 2.56 for the shear rate of 0.16 1/s,
10.06 and 2.18 for the shear rate of 0.25 1/s,
7.71 and 1.88 for the shear rate of 0.40 1/s,
5.99 and 1.65 for the shear rate of 0.63 1/s,
4.71 and 1.46 for the shear rate of 1.01 1/s,
4.08 and 1.32 for the shear rate of 1.62 1/s, and
2.89 and 1.09 for the shear rate of 2.59 1/s.

7. The method of claim 2, wherein the predetermined upper limit and the predetermined lower limit of the viscosity/elastic modulus measured for each shear rate are
47.17 and 6.67 for the shear rate of 0.03 1/s,
35.07 and 4.86 for the shear rate of 0.04 1/s,
25.37 and 3.77 for the shear rate of 0.06 1/s,
18.40 and 3.06 for the shear rate of 0.10 1/s,
13.47 and 2.56 for the shear rate of 0.16 1/s,
10.06 and 2.18 for the shear rate of 0.25 1/s,
7.71 and 1.88 for the shear rate of 0.40 1/s,
5.99 and 1.65 for the shear rate of 0.63 1/s,
4.71 and 1.46 for the shear rate of 1.01 1/s,
4.08 and 1.32 for the shear rate of 1.62 1/s, and
2.89 and 1.09 for the shear rate of 2.59 1/s.

8. The method of claim 5, wherein the predetermined upper limit and the predetermined lower limit of the viscosity/elastic modulus measured for each shear rate are
47.17 and 6.67 for the shear rate of 0.03 1/s,
35.07 and 4.86 for the shear rate of 0.04 1/s,
25.37 and 3.77 for the shear rate of 0.06 1/s,
18.40 and 3.06 for the shear rate of 0.10 1/s,
13.47 and 2.56 for the shear rate of 0.16 1/s,
10.06 and 2.18 for the shear rate of 0.25 1/s,
7.71 and 1.88 for the shear rate of 0.40 1/s,
5.99 and 1.65 for the shear rate of 0.63 1/s,
4.71 and 1.46 for the shear rate of 1.01 1/s,
4.08 and 1.32 for the shear rate of 1.62 1/s, and
2.89 and 1.09 for the shear rate of 2.59 1/s.

* * * * *